United States Patent [19]

Fischer et al.

[11] Patent Number: 4,711,232

[45] Date of Patent: Dec. 8, 1987

[54] BONE FASTENER AND METHOD OF INSTALLING SAME

[75] Inventors: Artur Fischer, Weinhalde 34, D-7244 Waldachtal 3; Wolfgang Kramer, Oberjettingen, both of Fed. Rep. of Germany

[73] Assignee: Artur Fischer, Waldachtal, Fed. Rep. of Germany

[21] Appl. No.: 813,224

[22] Filed: Dec. 23, 1985

[30] Foreign Application Priority Data

Jul. 12, 1985 [DE] Fed. Rep. of Germany ....... 3524946

[51] Int. Cl.$^4$ .................................................. A61F 5/04
[52] U.S. Cl. .............................. 128/92 YF; 411/57; 411/71; 411/395; 128/92 YE
[58] Field of Search ............ 128/92 R, 92 YF, 92 YP, 128/92 YE; 411/57, 60, 71, 72, 178, 395

[56] References Cited

U.S. PATENT DOCUMENTS

| | | | |
|---|---|---|---|
| 1,021,390 | 3/1912 | Wagner | 411/57 |
| 1,136,638 | 4/1915 | Zifferer | 411/60 |
| 1,138,219 | 5/1915 | Hottenroth | 411/57 |
| 1,922,120 | 8/1983 | Brosig | 411/60 |
| 2,026,686 | 1/1936 | Kirley | 411/57 |
| 2,370,327 | 2/1945 | Rosan | 411/57 |
| 2,455,885 | 12/1948 | Theurer | 411/57 |
| 2,871,749 | 2/1959 | Kalb | 411/57 |
| 3,022,701 | 2/1962 | Potruch | 411/57 |
| 3,081,808 | 3/1963 | Rosan et al. | 411/178 |
| 3,230,994 | 1/1966 | Rosan | 411/178 |
| 3,279,519 | 10/1966 | Neuschotz | 411/178 |
| 3,281,173 | 10/1966 | Rosan | 411/178 |
| 3,383,975 | 5/1968 | Cushman | 411/57 |
| 3,413,887 | 12/1968 | Von Wolff et al. | 411/60 |
| 3,435,526 | 4/1969 | Brancato | 128/92 YF |
| 4,011,602 | 3/1977 | Rybicki et al. | 128/92 YF |
| 4,408,938 | 10/1983 | Maguire | 411/57 |
| 4,484,570 | 11/1984 | Suther et al. | 128/92 YP |
| 4,488,843 | 12/1984 | Achille | 411/60 |

*Primary Examiner*—C. Fred Rosenbaum
*Assistant Examiner*—C. W. Shedd
*Attorney, Agent, or Firm*—Michael J. Striker

[57] ABSTRACT

A fastener for anchoring in a bore in a bone has a screw having a substantially cylindrical outer surface formed with a helical screwthread. This screw has at its screwthread a thread diameter and between the turns of the thread at the surface a root diameter smaller than the thread diameter. A synthetic-resin anchor sleeve of a resilient fitted in the bore is of an outside diameter corresponding generally to the diameter of the bore and has an outer end formed with an outwardly open polygonal-section recess, an inner end formed with an inwardly open and transversely throughgoing slot, an outer end portion of an inside diameter greater than the root diameter but smaller than the thread diameter, an inner end portion of an inside diameter smaller than the root diameter, and an external helicoidal screwthread extending about two-thirds of the length of the sleeve from its inner end toward its outer end.

4 Claims, 3 Drawing Figures

BONE FASTENER AND METHOD OF INSTALLING SAME

FIELD OF THE INVENTION

The present invention relates to a bone fastener. More particularly this invention concerns a sleeve-and-screw fastener and method of using same.

BACKGROUND OF THE INVENTION

A standard orthopedic procedure, for instance to splint the lateral portion of the distal tibia, entails reducing the fracture, drilling at least one hole to each side of the fracture, and then securing a plate across the fracture with screws. Similarly it is known, for example to fix a fragment of a broken medial malleolus, to drill a hole through the fragment into the bone and secure the fragment in place with a screw. The type of screw used depends on the type of bone tissue it will have to hold in. Cortical screws are intended to hold at the hard outer cortex of the bone while cancellous screws hold in the soft interior of the bone.

Thus a cancellous screw has a very deep screwthread intended to bite into the spongy interior of the bone. Unfortunately, once the fracture has knitted, this type of screw is fairly difficult to remove due to the adhesion of the spongy bone to its considerable surface area and the normally good adherence of bone to metal. In addition the hold of such a screw is frequently poor since the material it is holding in has little elasticity. Thus when stressed the screw either holds solidly or comes completely loose. The screw can loosen or pull out if stressed beyond a predetermined relatively low limit, there being no elasticity to the connection.

Accordingly a bone fastener is known that uses a synthetic-resin sleeve that is set into a hole bored in the bone, and then the screw is threaded into this sleeve. The result is a somewhat elastic connection, but the hold of the sleeve is often poor, at least until the screw is installed in it. In addition use of such a system is often somewhat cumbersome.

OBJECTS OF THE INVENTION

It is therefore an object of the present invention to provide an improved bone fastener.

Another object is the provision of such a bone fastener which overcomes the above-given disadvantages, that is which holds solidly while permitting the connection to give or work a little, and which is easy to use.

A further object is to provide an improved method of fastening to a bone, in particular of securing a splint plate.

SUMMARY OF THE INVENTION

A fastener for anchoring in a bore in a bone according to the invention has a screw having a substantially cylindrical outer surface formed with a helical screwthread. This screw has at its screwthread a thread diameter and between the turns of the thread at the surface a root diameter smaller than the thread diameter. A synthetic-resin anchor sleeve of a resilient fitted in the bore is of an outside diameter corresponding generally to the diameter of the bore and has an outer end formed with an outwardly open polygonal-section recess, an inner end formed with an inwardly open and transversely throughgoing slot, an outer end portion of an inside diameter greater than the root diameter but smaller than the thread diameter, an inner end portion of an inside diameter smaller than the root diameter, and an external helicoidal screwthread extending about two-thirds of the length of the sleeve from its inner end toward its outer end.

Thus the sleeve can be fitted to a standard hex key or screwdriver so it can be threaded into the bore. This means that the sleeve is fairly well anchored even before the screw is driven into it to swell its inner portion and lock it even better in the bore. Similarly the sleeve can be screwed back out of the bone once the fracture has healed, a procedure that is much gentler on the patient than the standard procedure of pulling the sleeve straight out.

According to another invention feature the sleeve is provided on its outer portion with a covering of metal or other X-ray blocking material. This makes it visible to an X-ray so its position and/or presence can be ascertained accurately. In addition the screwthread of the sleeve has a rounded outer edge and the outer surface is rounded between the turns thereof. This minimizes damage to the bone tissue.

The method of this invention comprises the steps of first boring in the bone a hole of a diameter corresponding generally to the outer diameter of the sleeve and then tapping the hole to have an internal screwthread substantially complementary to the thread of the sleeve. The sleeve is then screwed into the tapped hole with the thread of the sleeve mating with that of the hole, which operation is carried out by fitting a tool such as a hex key in the outer polygonal recess of the sleeve. A screw is then turned into the sleeve in the hole to expand the inner end portion of the sleeve.

According to a further feature of this invention the bore is tapped with a tool having a small-diameter tip formed with a cutting thread and with a larger-diameter shank formed with a smoothing and forming thread substantially identical to the thread of the sleeve. The cutting thread is about 10% smaller in cross-sectional size than the smoothing thread. In this manner the internal screwthread is formed first by being cut into the hole with the cutting thread and then by being enlarged and smoothed by the smoothing thread. The result is a very good and solid contact surface for the screwthread of the sleeve, as the soft bone tissue inside the bone is densified at the internal screwthread when it is formed this way.

In addition when the screw is screwed into the sleeve it is threaded into and completely through the sleeve so the thread cuts into the outer portion without substantially deforming and spreading same and into the inner portion with substantial outward deformation and spreading of same. As a result the radial engagement of the inner portion with the bone solidly secures the sleeve in the bone while the engagement of the threads in the sleeve solidly secures the screw in the sleeve. When the sleeve is subsequently screwed out of the bone the inner portion will deform inward and allow the sleeve to pass out of the bore.

The screw of this invention is typically used to secure a splint plate that is positioned over the sleeve on the bone after screwing the sleeve into the bore and screwing the screw through the plate into the sleeve. Such a splint plate will be very solidly held.

DESCRIPTION OF THE DRAWING

The above and other features and advantages will become more readily apparent from the following, reference being made to the accompanying drawing in which.

SPECIFIC DESCRIPTION

Figure 1:
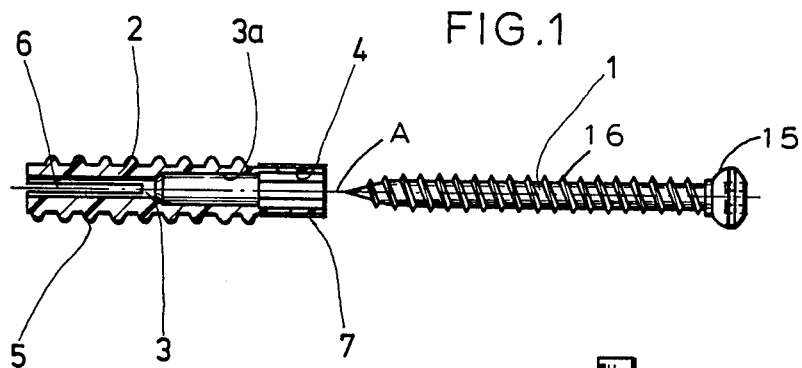
FIG. 1 is an exploded view of the fastener according to the invention partly in axial section.

As seen in FIG. 1 a bone fastener system basically comprises a stainless-steel screw 1 and an anchor sleeve 2 of polyethylene of ultrahigh molecular weight. The screw 1 is centered on an axis A and has a cylindrical shaft formed with a sharp-edged screwthread 16. The shaft and thread 16 respectively define a shaft diameter and a larger thread diameter. The tip of the screw 1 is pointed and the opposite outer end of the screw 1 has a head 15 formed with an outwardly open hexagonal recess centered on the axis A.

The sleeve 2 is also centered on the axis A and has an outer end formed with another hexagonal-section recess 4 which may be the same size as or larger than that of the head 15. In addition the sleeve 2 has inward of the hex recess 4 an outer portion 3a with an inner surface of a diameter greater than the diameter of the thread 16 but smaller than the shaft diameter between the turns of the thread 16 and an inner portion 3 with a cylindrical inner surface with a diameter smaller than the screw-shaft diameter. The extreme inner end of the sleeve 2 is formed with a radially throughgoing and axially inwardly open split 6 extending about four-fifths the axial length of the small-diameter inner portion 3 of the sleeve 2, which itself accounts for about half the sleeve's length.

In addition the sleeve 2 is formed over its inner two-thirds with a helical round screwthread 5 and is provided on the outer half of its inner portion 3 with a cladding 7 of stainless steel. This cladding 7 can be formed by a sleeve retrofitted to the outer sleeve portion 3a or by vacuum deposition thereon. It makes the sleeve 2 visible to X-rays, so its position and/or presence can be checked easily.

Figure 2:
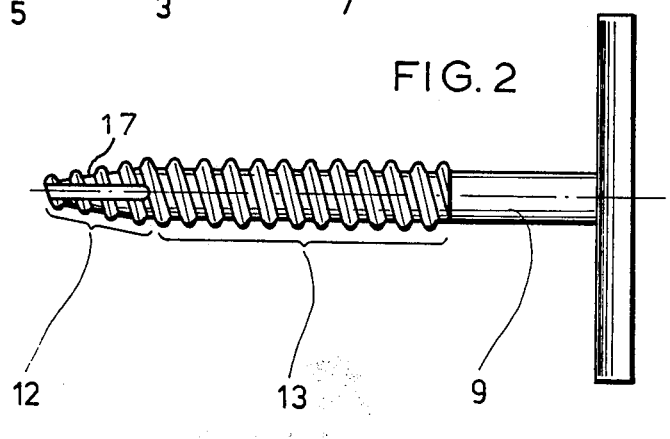
FIG. 2 is a side view of the tapping tool according to this invention.

In FIG. 2 a tapping tool is 9 is shown having a screwthread with a small-size front portion 12 and a full-size rear portion 13. A chip flute 17 at the front end of the tool 9 assists in the cutting carried out here. The thread 13 is complementary to the thread 5.

Figure 3:
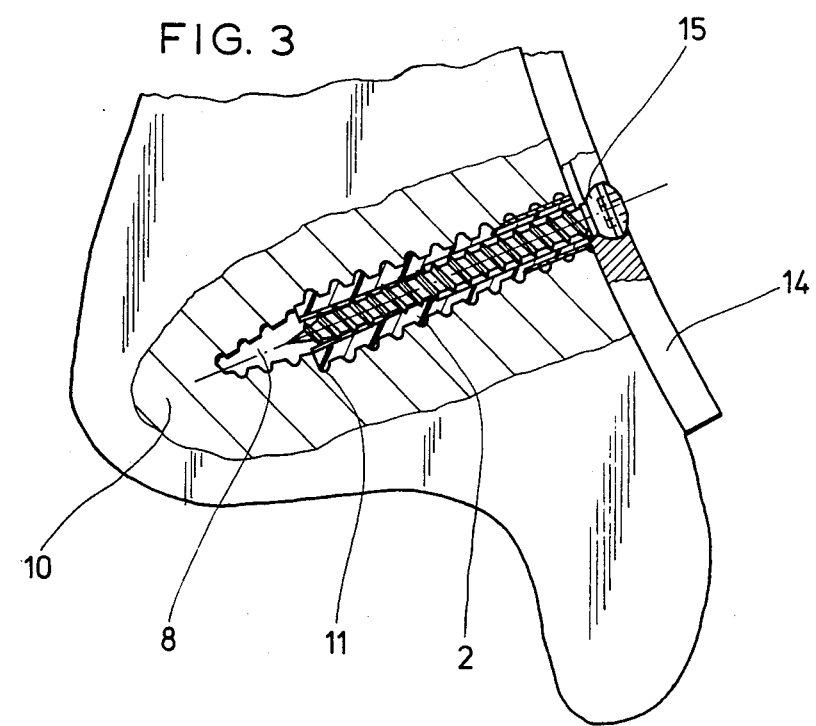
FIG. 3 is a partial section illustrating the fastener in use.

Thus in use a bone such as shown at 10 in FIG. 3 is drilled out to have a hole 8 of a diameter correspondingly to the shaft diameter of the sleeve 2. Then the tool 9 is screwed into this bore 8, cutting in it a screwthread 11 perfectly complementary to the thread 5. The cutting threads 12 are about 10% undersized, that is axially and radially shorter. Thus the threads 13 smooth and compress the undersized internal thread 11, giving it a smooth and compact surface.

Then as further shown in FIG. 3 the sleeve 2 is installed in the bore 8 by fitting a hex key to the recess 4 and screwing the sleeve 2 in until it is flush with the bone surface. Such installation is particularly easy on the smoothed screwthread 11. When thus installed the wrench can be pulled out of the recess, leaving the sleeve 2 solidly in place. When the screw 1 is then threaded into the sleeve 2, its thread 16 bites slightly into the outer portion 3a without substantial outward deformation of this portion 3a. When, however, the screwthread 16 bites into the inner sleeve portion 3 it swells it substantially outward, forcing the screw thread 5 into excellent radial contact with the spongy interior of the bone 10. As a result there is excellent connection and holding of the screw 1 and sleeve 2 in the bore 8.

The tip of the screw 1 passes out the extreme inner end of the sleeve 2, spreading it at the split 6. The head 15 comes to lie against the outer face of a splint plate 14 here securing the medial malleolus on the bone 10. The resultant assembly is extremely strong, yet elastic enough that it has some give. Thus if momentarily stressed very greatly, the sleeve 2 will deform rather than the screw 1 tearing out.

To remove the assembly the screws 1 are backed out and the plate 14 removed. Then the hex key is fitted into the recess and the sleeve 2 is screwed back out of the hole 8. This action will pull out the sleeve 2, as the spread but empty inner portion 3 can easily deflect back inward.

We claim:

1. In a combination comprising a fastener and a threaded bore in a bone in which the fastener is anchored, the fastener being utilizable with hard and soft bones and comprising:

a screw having a substantially cylindrical outer surface formed with a helical srewthread, the screw having at its screwthread a thread diameter and between the turns of the thread at the surface a root diameter smaller than the thread diameter; and an anchor sleeve of a resilient synthetic resin, defining and extending along an axis, normally fitted in the bore, of an outside diameter corresponding generally to the diameter of the bore, and having an outer end formed with an outwardly open polygonal-section recess, an inner end formed with an inwardly open and transversely throughgoing slot, an outer end portion of an inside diameter greater than the root diameter but smaller than the thread diameter, an inner end portion of an inside diameter smaller than the root diameter, and an external helicoidal screwthread extending about two-thirds of the length of the sleeve from its inner end toward its outer end, the screwthread of the sleeve having a rounded outer edge and the outer surface being rounded between the turns thereof.

2. The bone fastener defined in claim 1 wherein the sleeve is provided on its outer portion with a covering of metal.

3. A fastener for anchoring in a bore in a bone, the fastener comprising:

a screw having a substantially cylindrical outer surface formed with a helical screwthread, the screw having at its screwthread a thread diameter and between the turns of the thread at the surface a root diameter smaller than the thread diameter; and an anchor sleeve of a resilient synthetic resin, defining and extending along an axis, normally fitted in the bore, of an outside diameter corresponding generally to the diameter of the bore, and having an outer end formed with an outwardly open polygonal-section recess, an inner end formed with an inwardly open and transversely throughgoing slot, an outer end portion of an inside diameter greater than the root diameter but smaller than the thread diameter, an inner end portion of an inside diameter small than the root diameter, and an external helicoidal screwthread extending about two-thirds of the length of the sleeve from its inner end toward its outer end, the sleeve being provided on its outer portion with a covering of metal.

4. The bone fastener defined in claim 3, wherein the screwthread of the sleeve has a rounded outer edge and the outer surface is rounded between the turns thereof.

* * * * *